United States Patent
DeGrandpre et al.

(10) Patent No.: US 9,562,881 B2
(45) Date of Patent: Feb. 7, 2017

(54) TITRATION METHOD USING A TRACER TO QUANTIFY THE TITRANT

(76) Inventors: Michael D. DeGrandpre, Missoula, MT (US); Todd Martz, Aptos, CA (US); Andrew Dickson, San Diego, CA (US)

(*) Notice: Subject to any disclaimer, the term of this patent is extended or adjusted under 35 U.S.C. 154(b) by 1096 days.

(21) Appl. No.: 11/698,594

(22) Filed: Jan. 26, 2007

(65) Prior Publication Data
US 2007/0231910 A1 Oct. 4, 2007

Related U.S. Application Data

(60) Provisional application No. 60/763,170, filed on Jan. 26, 2006.

(51) Int. Cl.
*G01N 31/16* (2006.01)
*G01N 31/22* (2006.01)

(52) U.S. Cl.
CPC .............. *G01N 31/22* (2013.01); *G01N 31/16* (2013.01); *G01N 31/166* (2013.01); *Y10T 436/13* (2015.01)

(58) Field of Classification Search
CPC ...... G01N 33/18; G01N 33/84; G01N 33/582; G01N 33/1853; G01N 33/54373; G01N 33/0013; G01N 33/1826; G01N 31/22; G01N 31/16; G01N 31/162; G01N 31/164; G01N 31/166; G01N 31/221; G01N 21/78; G01N 21/80; G01N 21/274; G01N 2021/7786; G01N 27/44
See application file for complete search history.

(56) References Cited

U.S. PATENT DOCUMENTS

| | | |
|---|---|---|
| 4,798,803 A | 1/1989 | Wolcott et al. |
| 5,618,495 A | 4/1997 | Mount et al. |
| 6,004,822 A | 12/1999 | Li et al. |
| 6,082,204 A | 7/2000 | Munderloh |
| 6,913,672 B2 | 7/2005 | Hsu |
| 6,913,930 B2 | 7/2005 | Bevan et al. |
| 2004/0023405 A1 | 2/2004 | Bevan et al. |

OTHER PUBLICATIONS

Titration Equation for Polyprotic Acids, 2004, http://www.chem.usu.edu/%7Esbialkow/Classes/3600/Overheads/nHtitr/nHtitr.html.*
Van Oort et al. "A New Device for Automated Spectrophotometric Set-Point Titrations Comprising an Automatic Correction for Turbidity and Dilution Errors and Its Applications", Z. Anal. Chem., 1975, v. 276, pp. 177-180.*

(Continued)

*Primary Examiner* — Yelena G Gakh
(74) *Attorney, Agent, or Firm* — Lisa V. Mueller; Michael Best & Friedrich LLP (57) ABSTRACT

A titration method uses a tracer in the titrant or titrand to quantify the amount of titrant added. The method does not require quantitative addition of titrant or sample. The tracer can be inert or can participate as an indicator of the titrant-analyte reaction. If the tracer is inert, an alternative method for monitoring the progress of the titration is required. The tracer concentration is quantified by an appropriate method depending upon the type of tracer and analytical performance desired (e.g. precision, accuracy). The method simplifies titrations because it eliminates the need for a precision dispensing device and analytical balance.

20 Claims, 6 Drawing Sheets

(56) References Cited

OTHER PUBLICATIONS

G. den Boef et al."Photometric Titration of Metal Ions, Based on Ultraviolet Absorption by a Lead(II) Complex. I", Mikroehimiea Aeta [Wien] 1971, pp. 366-370.*

Benaim et al. "Simple Fibre Optic pH Sensor for Use in Liquid Titrations", Analyst, 1986, vol. 111, pp. 1095-1097.*

Powell et al. "Self-indicating Flow Visible Spectrophotometric Titrations in a Variable-volume Tank Reactor", Analyst, 1991, vol. 116, pp. 631-640.*

Dantan et al. "comparison of spectrophotometric and potentiometric detection for the determination of water using Karl Fischer method under flow injection analysis conditions", Analytica Chimica Acta, 2000, v. 420, pp. 133-142.*

"Acid Base Titration Lab Exam Tutorial" http://http-server.carleton.ca/~rburk/chem1000/tutorials/tut18-02.htm, no date.*

Titrations, http://www.chemistry.nmsu.edu/studntres/chem116/notes/titrations.html, no date.*

Martz et al. "A Submersible Autonomous Sensor for Spectrophotometric pH Measurements of Natural Waters", Anal. Chem. 2003, v. 75, pp. 1844-1850.*

"Dilution Tecniques & Calculations" http://www.protocol-online.org/biology-forums/posts/22485.html, pp. 1-6, 1999-2008.*

Roche, Mary P., Measurement of total alkalinity of surface waters using a continuous flowing spectrophotometric technique, 1998, 85-94, Marine Chemistry 60, Elsevier Science.

Dickson, A.G., An extract definition of total alkalinity and a procedure for the estimation of alkalinity and total inorganic carbon from titration data, Deep-Sea Res., 1981, pp. 609-623, vol. 2 A, No. 6, Pergamon Press Ltd., Great Britain.

Clayton, T.D. et al., Spectorphotometric seawater pH measurements: total hydrogen ion concentration scale calibration of m-cresol purple and at-sea results, Deep-Sea Res.,1993, pp. 2115-2129, vol. 40, No. 10, Pergamon Press Ltd., Great Britain.

Korn, M. et al., Binary search in flow titration employing photometric end-point detection, Anal. Chim. Acta., 1995, pp. 177-184, vol. 313, Elsevier Sci. B.V.

Tanaka, H. et al., Continuous On-line True Titrations by Feedback-based Flow Ratiometry. The Principle of Compensating Errors, Anal. Chem, 2000, pp. 4713-4720, vol. 72, American Chemical Society.

Almeida, C.M.N.V. et al., An automatic titrator based on a multicommutated unsegmented flow system Its application to acid-base titrations, Anal. Chim. Acta., 2000, pp. 213-222, vol. 407, Elsevier Sci. B.V.

Fletcher, P.J. et al., Determination of carbonate and hydrogencarbonate by titration using sequential injection analysis, Anal. Chim. Acta., 2003, pp. 187-194, vol. 485, Elsevier Sci. B.V.

Watanabe, A. et al., A rapid, precise potentiometric determination of total alkalinity in seawater by a newly developed flow-through analyzer designed for coastal regions, Marine Chemistry, 2004, pp. 75-87, vol. 85, Elsevier Sci. B.V.

Martz, T.R. et al., Tracer Monitored Titrations: Measurement of Total Alkalinity, Anal, Chem., 2006, pp. 1817-1826, vol. 78, American Chemical Society.

Harris, D.C., Quantitative Chemical Analysis, 2007, pp. 128-130, 76th ed., W.H. Freeman, New York.

Harris, D.C., Quantitative Chemical Analysis, 2007, pp. 241-243, 76th ed., W.H. Freeman, New York.

Harris, D.C., Quantitative Chemical Analysis, 2007, pp. 332-335, 76th ed., W.H. Freeman, New York.

Jantsch T. G. et al. "An automated spectrophotometric system for monitoring buffer capacity in anaerobic digestion processes", Water Research 38 (2004) 3645-3650, the whole text.

Liao, Process monitored spectrophotometric titration coupled with chemometrics for simultaneous determination of mixtures of weak acids, Analytica Chimica Acta, 2007, 123-131, 591, Elsevier.

Degrandpre, Universal Tracer Monitored Titrations, Analytical Chemistry, 2011, 9217-9220, 83, ACS Publications.

Day et al., Quantitative Analysis, 6th ed., Prentice Hall, New Jersey, 1991.

Ruzicka, J. Flow Injection Analysis, 2nd ed., J. Wiley: New York, 1998.

Skoog et al., Principles of Instrumental Analysis, 5th ed., Harcourt & Brace, Chicago, 1998.

Carbon Dioxide Information Analysis Center (CDIAC), Global Ocean Data Analysis Project (GLODAP), http://cdiac.esd.oml.gov/oceans/glodap/Glodap_home.htm, webpage available as early as Jun. 22, 2002.

Metrohm Automated Titration Systems (MATi): "Titration on a whole new level: Discover OMNIS," www.metrohm.com, webpage available as early as Jun. 26, 2015.

Aragoni et al., "Characterization of the ionization and spectral properties of sulfonephthalein indicators. Correlation with substituent effects and structural features. Part II," Talanta, 1995, 42, 1157-1163.

Bates et al., "Alkalinity changes in the Sargasso Sea: geochemical evidence of calcification?," Mar. Chem. 1996, 51, 347-358.

Breland et al., "Spectrophotometric procedures for determination of sea water alkalinity using bromocresol green," Deep-Sea Res. I. 1993, 40, 629-641.

Byrne et al., "Seawater pH measurements: an at-sea comparison of spectrophotometric and potentiometric methods," Deep Sea Res. 1988, 35, 1405-1410.

Degrandpre et al., "In situ measurements of seawater pCO2," Limnol. Oceanog, 1995, 40, 969-975.

Dickson et al., "Handbook of methods for the analysis of the various parameters of the carbon dioxide system in sea water," Version 2, A. ORNL/CDIAC-74, 1994.

Dickson et al., "The Effect of Analytical Error on the Evaluation of the Components of the Aquatic Carbon-Dioxide System," Mar. Chem. 1978, 6, 77-85.

Dickson et al., "Reference materials for oceanic CO2 analysis: a method for the certification of total alkalinity," Mar. Chem. 2003, 80, 185-197.

Dickson, A. G., "Reference Materials for Oceanic CO2 Measurements," Oceanog, 2001, 14(4), 21-22.

Dyrssen et al., "Ionic Medium Effects in Sea Water—A Comparison of Acidity Constants of Carbonic Acid and Boric Acid in Sodium Chloride and Synthetic Sea Water," Mar. Chem. 1973, 1, 137-149.

Feely et al., "In situ calcium carbonate dissolution in the Pacific Ocean," Global Biogeochem. Cycles. 2002, 16, 91-1 — 1-12.

Gloor et al., "A first estimate of present and preindustrial air-sea CO2 flux patterns based on ocean interior carbon measurements and models," Geophys. Res. Leff. 2003, 30, 10-1 — 10-4.

Gruber et al., "An improved method for detecting anthropogenic CO2 in the oceans," Global Biogeochem. Cycles. 1996, 10, 809-837.

King et al., "Determination of Seawater pH from 1.5 to 8.5 using Colorimetric Indicators," Mar. Chem. 1989, 26, 5-20.

Langdon et al., "Effect of calcium carbonate saturation state on the calcification rate of an experimental coral reef," Global Biogeochem. Cycles. 2000, 14, 639-654.

Lazar et al., "Bioerosion of coral reefs—A chemical approach," Limnol. Oceanog., 1991, 36, 377-383.

Liang, Y. Y., "Automation of Karl Fischer Water Titration by Flow Injection Sampling," Anal. Chem. 1990, 62, 2504-2506.

Martz, T.R. PhD, "A Tracer Monitored Titration for Seawater Total Alkalinity," Thesis, University of Montana, 2005.

Millero et al., "Distribution of alkalinity in the surface waters of the major oceans," Mar. Chem. 1998, 60, 111-130.

Milliman et al., "Biologically mediated dissolution of calcium carbonate above the chemical lysocline?," Deep-Sea Res. I. 1999, 1653-1669.

Pankow, J.F., "Gran Titrations," Aquatic Chemistry Concepts, Ch. 10, Lewis, Chelsea, 1991.

Sabine et al., "The Oceanic Sink for Anthropogenic CO2," Science, 2004, 305, 367-371.

Suzuki et al., "Carbon budget of coral reef systems: an overview of observations in fringing reefs, barrier reefs and tolls in the Indo-Pacific regions," Tellus, 2003, 55B, 428-444.

(56) References Cited

OTHER PUBLICATIONS

Yao et al., "Simplified seawater alkalinity analysis: Use of linear array spectrometers," Deep-Sea Res. I. 1998, 45, 1383-1392.
International Search Report for Application No. PCT/US2007/002172 dated Nov. 19, 2007 (4 pages).
International Preliminary Report on Patentability for Application No. PCT/US2007/002172 dated Jul. 29, 2008 (7 pages).
Liao, Spectroscopy and Spectral Analysis, 2007, 27(12) 2601-2604, (English abstract).

* cited by examiner

TITRATION METHOD USING A TRACER TO QUANTIFY THE TITRANT

CROSS-REFERENCE TO RELATED APPLICATIONS

This application claims the benefits of U.S. Provisional Application No. 60/763,170, filed Jan. 26, 2006, the disclosure of which is hereby incorporated by reference in its entirety including all figures, tables and drawings.

STATEMENT REGARDING FEDERALLY SPONSORED RESEARCH OR DEVELOPMENT

The subject application was made with government support under a research project supported by the Office of Naval Research, Grant No. N00014-00-1-0573 and the National Science Foundation, Grant No. 0327763. The government has certain rights in this invention.

BACKGROUND OF THE INVENTION

There is great demand for simplified titrations for applications in industry, medicine, environmental monitoring and academic research. Simplified titration systems provide advantages because they can be more easily automated, they can be used by inexperienced operators, and they are less expensive. Conventional titration methods use volumetric glassware or analytical balances to quantify sample and burets or pipets to dispense titrant. Titration methods that use flow injection analysis, sequential injection analysis (Fletcher and van Staden, 2003), continuous on-line endpoint monitoring (Tanaka et al., 2000; Watanabe et al., 2004) and a variety of unsegmented batch titrations (Almeida et al., 2000; Korn et al., 1995), do not use discrete volumetric or gravimetric measurements but require very precise control of flow rate. These titrations use peak width measurements with a time abscissa or directly incorporate flow rate into the endpoint calculation and are therefore sensitive to variations in flow rate. To obtain the best data, high precision pumps must be used with repeated introduction of standards to compensate for pump fluctuations. There are heretofore no titration methods that do not rely on volumetric (either as a flowing stream or discrete volumes) or gravimetric analysis.

All patents, patent applications, provisional patent applications and publications referred to or cited herein, are incorporated by reference in their entirety to the extent they are not inconsistent with the explicit teachings of the specification.

SUMMARY OF THE INVENTION

The titration method of the subject invention quantifies the amount of titrant added to a sample by using a chemical or physical tracer in the titrant or equivalently, the titrand (sample). The titrant, quantified in this way, is then used in any of the conventional forms of titration data analysis (e.g. endpoint, Gran) to determine analyte concentration. The subject method can be used for all forms of titrations including a simple acid-base titration. The tracer is a quantifiable chemical species or physical property (e.g. scattering) and can be either inert or act as an indicator of the progress of a titration. The method of the subject invention does not require accurate nor precise volumetric or gravimetric addition of titrant; and additionally does not require accurate nor precise volumetric or gravimetric quantification of the titrand (sample).

DETAILED DESCRIPTION OF THE INVENTION

The titration method of the subject invention does not require quantitative volumetric or gravimetric measurement of titrant or titrand. The subject method uses a tracer to quantify the titrant added during the titration. Relative proportions of the tracer in the initial solution and in the titrant-titrand mixture are used to determine the reaction endpoint and analyte concentration. If the tracer is inert, an alternative method for monitoring the progress of the titration is required.

A physical or chemical tracer in the titrant or titrand (sample) is used to quantify the amount of titrant added to the titrand. The titrant, titrand (sample) and titrant-titrand mixture are denoted with the subscripts 'T', 'S', and 'mix' respectively. During any point in a conventional titration, the excess of titrant over analyte is represented by the simple mass balance $$\frac{[\text{titrant}]_T \times M_T - [\text{analyte}]_S \times M_S}{M_T + M_S} = [\text{titrant}]_{mix} - [\text{analyte}]_{mix} \quad (1)$$

where $[\text{titrant}]_T$ is the concentration of the titrant in the standardized titrant solution, $[\text{analyte}]_S$ is the analyte concentration in the sample, $M_T$ is mass or volume of titrant added, $M_S$ is sample mass or volume, and the subscript 'mix' denotes the equilibrium concentrations after mixing and neutralization. The equivalence point of a titration is the point where the equivalents of titrant added exactly equal the initial equivalents of analyte ($[\text{titrant}]_{mix}-[\text{analyte}]_{mix}=0$).

In a titration, titrant is added to sample to give a total mass or volume $M_{mix}$, $$M_{mix}=M_T+M_S. \quad (2)$$

Substitution of $M_{mix}$ into the left side of Equation 1 gives $$\frac{[\text{titrant}]_T \times M_T - [\text{analyte}]_S \times M_S}{M_{mix}} = [\text{titrant}]_T \frac{M_T}{M_{mix}} - [\text{analyte}]_S \frac{M_S}{M_{mix}}. \quad (3)$$

The mass or volume ratios in Equation 3 are the dilution factors of the titrant ($f_T$) and sample ($f_S$)

$$f_T = \frac{M_T}{M_{mix}} \text{ and } f_S = \frac{M_S}{M_{mix}}. \quad (4)$$

$$\text{or generally, } f = \frac{M}{M_{mix}} = \frac{[\text{tracer}]_{mix}}{[\text{tracer}]_I}$$

where M is mass or volume of titrant or titrand, $[\text{tracer}]_{mix}$ is the tracer concentration in the mixture, and $[\text{tracer}]_I$ is the initial tracer concentration in the titrant or titrand. Specifically, if the tracer is added to the titrant, the dilution factor $f_T$ is calculated from the ratio of titrant-based tracer concentration in the titration solution, $[\text{tracer}_{titrant}]_{mix}$, to the total tracer concentration in the titrant, $[\text{tracer}_{titrant}]_T$ (Equation 5). Similarly, if the tracer is added to the sample or pre-exists in the sample, e.g. a spectator ion, the dilution factor $f_S$ is calculated from the ratio of the tracer concentration in the titration solution, $[\text{tracer}_{titrand}]_{mix}$, to the total tracer concentration in the titrand (i.e. the sample), $[\text{tracer}_{titrand}]_S$ (Equation 5). Further, for either case the two dilution factors are related by $f_T + f_S = 1$.

$$f_T = \frac{M_T}{M_{mix}} \quad (5)$$

$$= \frac{[tracer_{titrant}]_{mix}}{[tracer_{titrant}]_T}$$

$$= \frac{[\text{titrant}]_{mix}}{[\text{titrant}]_T}$$

$$f_S = \frac{M_S}{M_{mix}}$$

$$= \frac{[tracer_{titrand}]_{mix}}{[tracer_{titrand}]_S}$$

$$= 1 - \frac{[\text{titrant}]_{mix}}{[\text{titrant}]_T}$$

Equation 5 illustrates how a tracer determines the amount of titrant added, $[\text{titrant}]_{mix}$. The dilution factor is determined by measurement of $[\text{tracer}]_{mix}$ and the known amount of tracer in the original titrant $[\text{tracer}_{titrant}]_T$ (or titrand). $[\text{titrant}]_{mix}$ is quantified using the dilution factor and the known concentration of titrant $[\text{titrant}]_T$.

Unlike the titrant and analyte, the tracer is neither consumed nor produced by chemical reaction. A tracer is defined as, but not necessarily limited to, 1) a single inert species that does not participate in the titration reaction, such as a spectator ion or molecule; 2) the sum of a family of chemical species, also referred to as the analytical concentration of a chemical; 3) any combination of chemical products and/or reactants that exhibits conservative behavior; 4) a physical property distinct to the titrant or sample, such as optical scattering by suspended particles.

Specifically, the tracer used in the method of the subject invention is a quantifiable chemical or physical species (e.g. an ion, an absorbing or fluorescent indicator or a light scattering particle) and can be either inert (e.g. a spectator ion) or act as an indicator of the progress of a titration (e.g. an acid-base indicator). For example, a spectrophotometric tracer can be either an inert chromophore or an indicator that is used to track the consumption of the analyte. If it is an indicator, all forms of that indicator must absorb light so that total indicator concentration can be quantified at any point in the titration from the sum of the different species (e.g. protonated+unprotonated; complexed+uncomplexed; reduced+oxidized). As an example, several redox indicators exhibit a color change from blue to red when reduced (Harris, 2007). Many metal ion indicators have light absorbing forms for both the free indicator and the indicator-metal ion complex (Harris, 2007).

If the tracer is inert, an alternative method for quantifying the equilibrium position of the titration is required. For example, an inert tracer can be detected using an ion-selective electrode to quantify the amount of titrant added while the pH of the titration solution is measured using a combination pH electrode. A physical mechanism such as turbidity could also function as a means to quantify titrant.

The initial tracer $[\text{tracer}]_I$ may be added to the titrant or titrand in a known amount (mass or volume) or can be quantified by measurement of the tracer concentration after addition of the tracer to the titrant or titrand or measurement of an existing natural tracer in the titrand (e.g. a spectator ion). If tracer is in the titrant, the measurement of $[\text{tracer}]_T$ is made when $f_T = 1$ (no titrand present). If the tracer is in the titrand, the measurement of $[\text{tracer}]_S$ is made when $f_S = 1$ (no titrant present). The measurements made when $f_T = 1$ or $f_S = 1$ are referred to as the chemical blank. In some titrands a natural tracer may exist and no tracer is added. In this case determination of $[\text{tracer}]_S$ when $f_S = 1$ is still required.

The method of the subject invention is applied to classical titration methodologies by substituting dilution factors for the typical volume or mass measurements in titration calculations. In most titrations, a titrant is added until an endpoint (ep) is achieved, as indicated by, for example, a change in a colored indicator. The endpoint corresponds approximately to the point where the equivalents of titrant added equal the equivalents of analyte in the titrand (the equivalence point), i.e. at the point where Equation 1 is equal to zero. In a classical titration, at the endpoint Equation 1 is solved for analyte concentration and the corresponding amount of titrant added, $M_T(ep)$, is used along with the known titrant concentration and sample mass (or volume):

$$[\text{analyte}]_S = [\text{titrant}]_T \frac{M_T(ep)}{M_S}. \quad (6)$$

For the subject method, the endpoint for Equation 3 is solved for analyte concentration and the corresponding dilution factor, $f_T(ep)$ is used with the known titrant concentration:

$$[\text{analyte}]_S = \frac{[\text{titrant}]_T}{1/f_T(ep) - 1} \quad (7)$$

Equation 7 is the equivalent of Equation 6, given that $f_T + f_S = 1$ for the method of the subject invention.

The following examples are offered to further illustrate but not limit the methods of the present invention.

EXAMPLE 1

Figure 1:
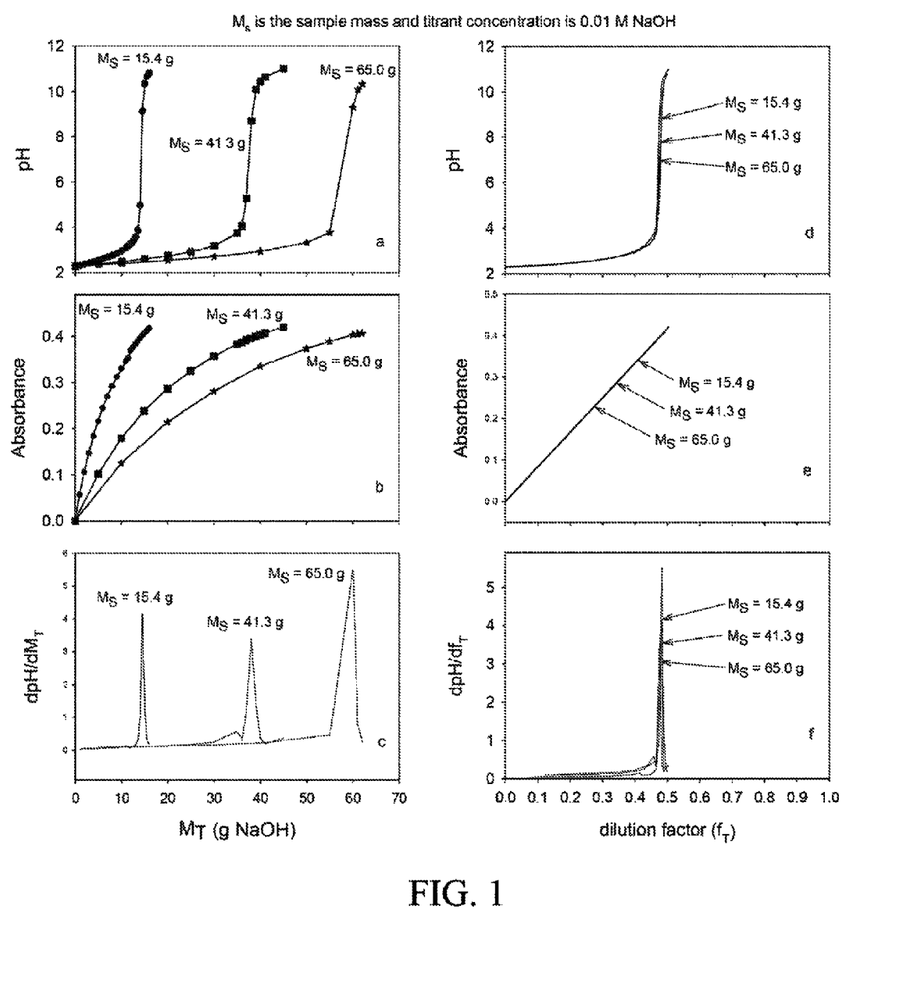
FIG. 1 shows data from the titration of 0.0089 M HCl with 0.0100 M NaOH in the conventional (on left) and using the method of the subject invention (on right) forms, as described in EXAMPLE 1.

Tracer Monitored Titration of Strong Acid by Strong Base Using an Inert Calorimetric Tracer and Potentiometric Endpoint Detection The example given here uses a glass combination pH electrode to follow the extent of the reaction of the titration and a colorimeter operating at a wavelength of 640 nm to follow the addition of titrant. In the classic potentiometric titration of HCl by NaOH, an electrode is placed in a known volume or mass of HCl. Standardized NaOH is added dropwise with a volumetric buret and pH and volume of titrant added are recorded for each titrant addition until the endpoint is reached. In contrast, the method of the subject invention does not require a known volume or mass of sample nor measured quantity of titrant. In the classical titration, the solution pH is plotted versus volume or mass of titrant added and from this plot the endpoint can be determined in a number of different ways—in this example by the first derivative of the pH vs volume curve. The analogue of the subject method plots dilution factor (Equation 5) on the x-axis instead of volume (or mass) of titrant. In this example, dilution factor is determined from a tracer added to the titrant ($[tracer_{titrant}]_T$) and the tracer concentration in the titrant-titrand mixture ($[tracer_{titrant}]_{mix}$) (Equation 5). FIG. 1 presents experimental data for a titration of 0.0089 M HCl by 0.0100 M NaOH. To demonstrate that the subject method is independent of sample (titrand) and titrant mass or volume, different masses were analyzed ($M_S$) (FIG. 1a,b). Data such as those shown in FIG. 1d-f were collected by (1) adding a quantitative amount of a pH insensitive dye brilliant blue with known molar absorptivity at a specified wavelength (640 nm in FIG. 1) to the titrant (0.0100 M NaOH); (2) pouring an unmeasured amount of sample (0.0089 M HCl) into a stirred beaker; (3) placing a pH electrode connected to a potentiometer and an optical dip probe connected to a single wavelength colorimeter in the HCl (4) Adding small, non-quantitative amounts of the titrant mixture to the HCl and recording electrode pH and optical absorbance after each addition. The tracer concentration, quantified by the optical absorbance, is used in Equation 5 to calculate the dilution factor. In the plots in FIG. 1 showing the subject method, the endpoint point was always located at the same dilution factor $f_T$, regardless of the initial sample size, while in the plot's of the conventional titration, the endpoint point changes with the initial sample size (compare FIGS. 1a,c and 1f).

After using a plot such as shown in FIG. 1f to determine $f_T$ at the endpoint, calculation of analyte concentration is similar to the classical computation. The dilution factor at the endpoint is used in Equation 7 to calculate analyte concentration. By this method, the concentration of HCl found for the three titrations shown in FIG. 1 is 0.093±0.002 mol kg$^{-1}$ (2% precision). Endpoints determined from the classical method (recorded masses and pH) (FIG. 1c) and used in Equation 6, yield similar precision (~1%). The subject method data shown in FIG. 1 represent excellent performance for many applications, accomplished without quantitative measurement of titrant or titrand.

EXAMPLE 2

Acid-Base Tracer Monitored Titration Using a Calorimetric pH Indicator as a Tracer and for Endpoint Detection In the present example, a pH indicator assumes the dual role of both titrant tracer and pH detector eliminating the need for a potentiometric pH meter and electrode (see Example 1). While a single wavelength colorimeter is sufficient to track an inert tracer (see Example 1), at least two wavelengths are required for accurate indicator pH measurements (see e.g. Clayton and Byrne, 1993) and to quantify the total indicator concentration, [tracer]mix for use in Equation 5 (Martz et al., 2006). Therefore, when using an acid-base pH indicator in place of the pH electrode, spectrophotometry provides all measurements necessary to calculate the analyte concentration and solution pH.

In this example, the subject method was used to determine seawater total alkalinity ($A_T$) (Martz et al., 2006). Because this application requires very good analytical precision and accuracy, more sophisticated data analysis was used than that described in Example 1. The analytical quantity, total alkalinity ($A_T$), was determined from a set of pH and dilution factor data using a non-linear least squares calculation as done with classical seawater $A_T$ titrations (Dickson, 1981).

Individual concentrations of each form of the indicator were required for each titration point in order to calculate the total tracer concentration, dilution factors and pH of the solution. The indicator, bromocresol green (BCG), used for this example is a diprotic molecule with $pK_{a1} < 0$ and $pK_{a2} \sim 4.5$, where $K_{a1}$ and $K_{a2}$ are the first and second dissociation constants, respectively $$HI^- \Leftrightarrow H^+ + I^{2-}. \tag{8}$$

Above a pH of ~0, only the second dissociation is important. The equilibrium and mass balance equations are $$K_a = \frac{[H^+][I^{2-}]}{[HI^-]} \tag{9}$$

$$[tracer] = [HI^-] + [I^{2-}] \tag{10}$$

where $K_a$ is the second dissociation constant ($K_{a2}$), [tracer] is the total tracer concentration in either the titrant or titrant-titrand mixture, [HI$^-$] is the singly protonated indicator concentration and [I$^{2-}$] is the fully deprotonated indicator concentration. The titrant contained a known amount of BCG so $[tracer_{titrant}]_T$ is known, and $[tracer_{titrant}]_{mix}$ is calculated from absorbance data for each titration point.

Figure 2:
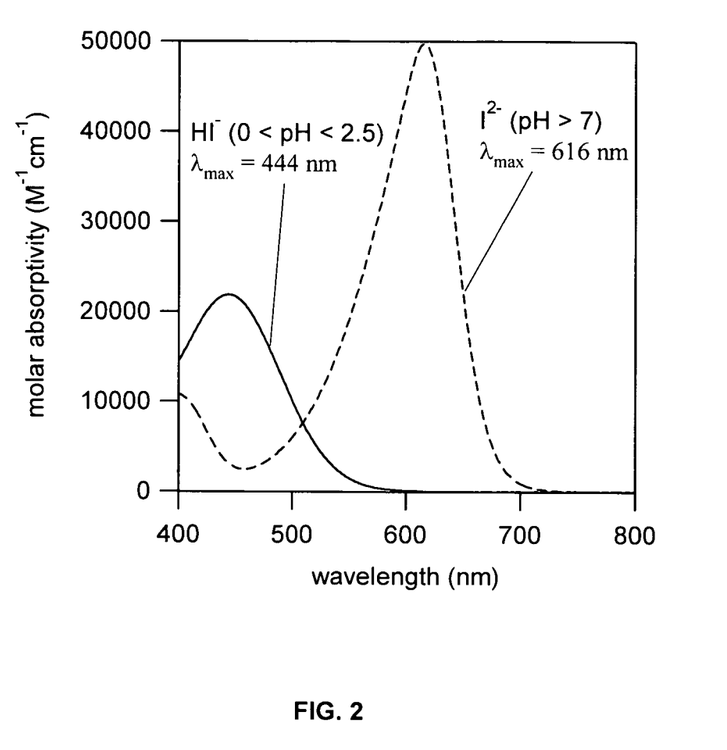
FIG. 2 shows the absorbance spectra of singly protonated and fully deprotonated bromocresol green, the indicator utilized in EXAMPLE 2.

Absorbance (A) at a particular wavelength ($\lambda$) is given by $$_\lambda A = _\lambda \epsilon_{HI} b [HI^-] + _\lambda \epsilon_I b [I^{2-}] \tag{11}$$

where $\epsilon$ is the molar absorptivity of each species at wavelength $\lambda$ and b is the pathlength. In general, the indicator spectra overlap and therefore $_\lambda A$ has contributions from both forms at each analytical wavelength. The indicator species were calculated using Equation 11 at two wavelengths (444 and 616 nm) corresponding to the absorbance maxima ($\lambda_{max}$) of HI$^-$ and I$^{2-}$ (FIG. 2), $$[HI^-] = \frac{_{444}A \, _{616}\epsilon_I b - _{616}A \, _{444}\epsilon_I b}{_{444}\epsilon_{HI} b \, _{616}\epsilon_I b - _{444}\epsilon_I b \, _{616}\epsilon_{HI} b} \tag{12a}$$

$$[I^{2-}] = \frac{_{616}A \, _{444}\epsilon_{HI} b - _{444}A \, _{616}\epsilon_{HI} b}{_{616}\epsilon_I b \, _{444}\epsilon_{HI} b - _{444}\epsilon_I b \, _{616}\epsilon_{HI} b}. \tag{12b}$$

Equations 12a and 12b are used with Equation 9 to calculate [H$^+$] and with Equation 10 to calculate $[tracer_{titrant}]_{mix}$. $[tracer_{titrant}]_{mix}$ and $[tracer_{titrant}]_T$ are then used with Equation 5 to obtain the dilution factor, $f_T$. These calculations require accurate $K_a$, $\epsilon$, and optical pathlength.

Methods—

Na$_2$CO$_3$ and NaOH test samples were prepared to $A_T \sim 0.0020$-0.0026 mol kg-soln$^{-1}$. Titrant was prepared to give [H$^+$]~2.4×10$^{-3}$ mol kg-soln$^{-1}$ and $[BCG]_T \sim 6.5 \times 10^{-5}$ mol kg-soln$^{-1}$. Test samples and titrant were prepared with a background matrix of NaCl to give ionic strength equal to 0.700.

Figure 3:
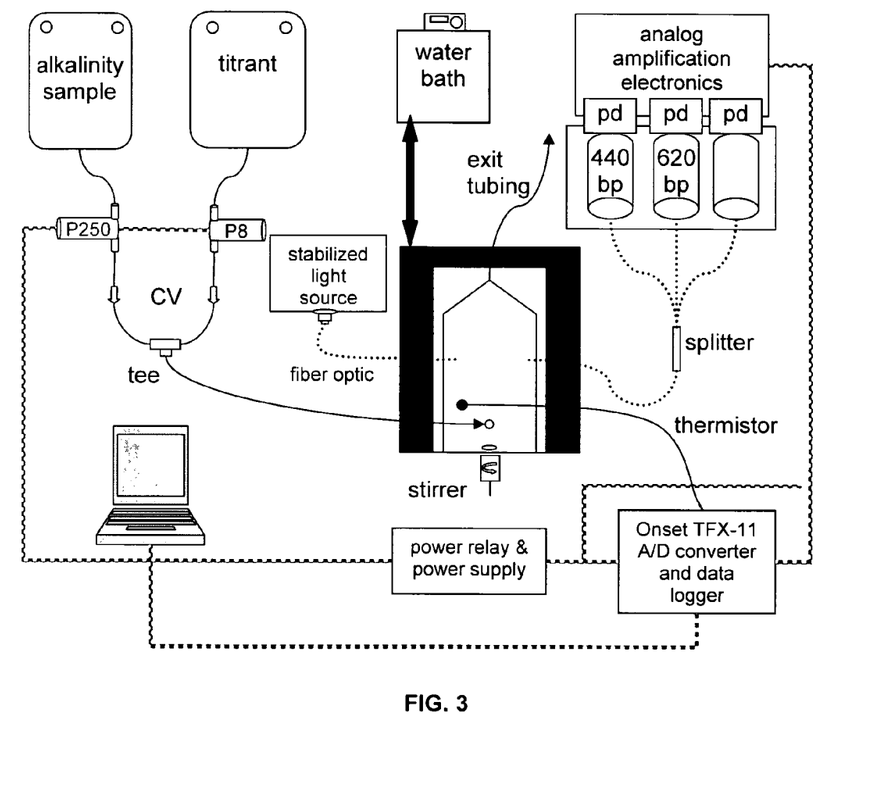
FIG. 3 is a diagrammatic representation of a titration apparatus described in EXAMPLE 2.

Solutions were titrated with the setup shown in FIG. 3. This apparatus is not required to execute the method of the subject invention but is required for its seawater $A_T$ application. Batch measurements are fully automated, requiring an operator only to reload samples. Sample and titrant bags are connected to 250 µL and 8 µL per pulse solenoid pumps, respectively. Pumps are pulsed on 0.5 sec (pretitration) or 1 sec (titration) intervals for titrant and 2 second intervals for sample, with a short delay (~0.5 sec) between each titrant pulse and detector reading. The pump outlets merge at a low dead volume tee, which connects to the inlet of a stirred optical flow cell with ~5 mL internal volume.

A three wavelength detection system was used. The optical system consists of a tungsten-halogen source, 1000 µm core fused silica fiber optics, a 3-way fiber optic bundle splitter, and a three channel spectrophotometer built from dual bandpass filters and Si photodiodes interfaced to a custom-built amplifier board. Optical interference filters were selected to match peak absorbance wavelengths of BCG as closely as possible (440 nm and 620 nm CWL filters for $\lambda_{max}$ at 444 nm and 616 nm, respectively; FIG. 2). The photocurrent from each photodiode (pd) was amplified using a two-stage inverting op-amp design. The resulting voltage was then digitized and logged by the data logger (TFX-11). Water bath temperature is set at 22.0° C. and connected to a built-in manifold in the flow cell. The temperature of the titration mixture was also directly monitored by a thermistor. A magnetic stir bar was sealed into the flow cell by an acrylic base plate, with a stirring motor mounted directly below.

Accuracy and precision were evaluated with the high salinity alkaline standards described above. The titration data were imported into Excel for calculation of $A_T$.

Titration Data—

Figure 4:
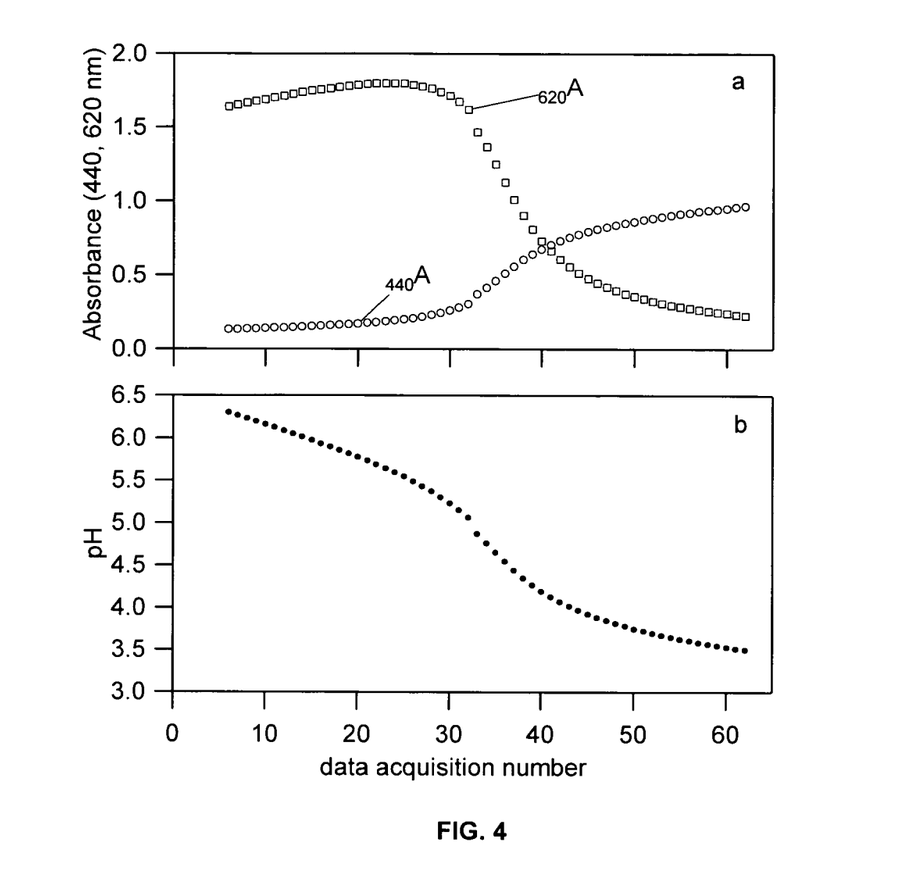
FIG. 4 presents experimental data illustrating measurement profiles for a single tracer monitored titration described in EXAMPLE 2.

FIG. 4a shows the absorbance data collected at the two wavelengths during a single titration. Blank data, when no indicator is present, are not shown because the noise (±0.0001) is not readable on the scale shown in FIG. 4a. Indicator species are calculated using Equation 12. [H$^+$] is calculated from Equation 9. Following FIG. 4b, a large pretitration pulse brings the titration solution to a pH of 6.0-6.5. At this pH the absorbance is high at 616 nm (I$^{2-}$ form) and low at 440 nm (HI$^-$ form) (FIG. 2, FIG. 4a). As titrant is added, the decreasing pH reflects the increasing acidity of the mixture inside the flow cell.

Total Alkalinity Replicates: Accuracy and Precision—

Figure 5:
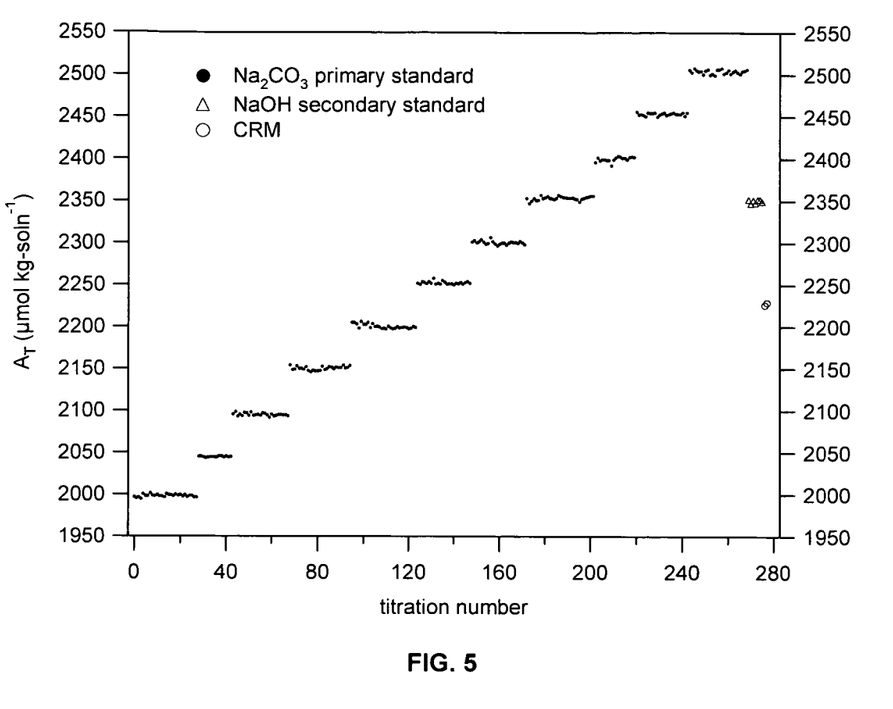
FIG. 5 presents results from 279 titrations spanning a range of total alkalinity as described in EXAMPLE 2.
Figure 6:
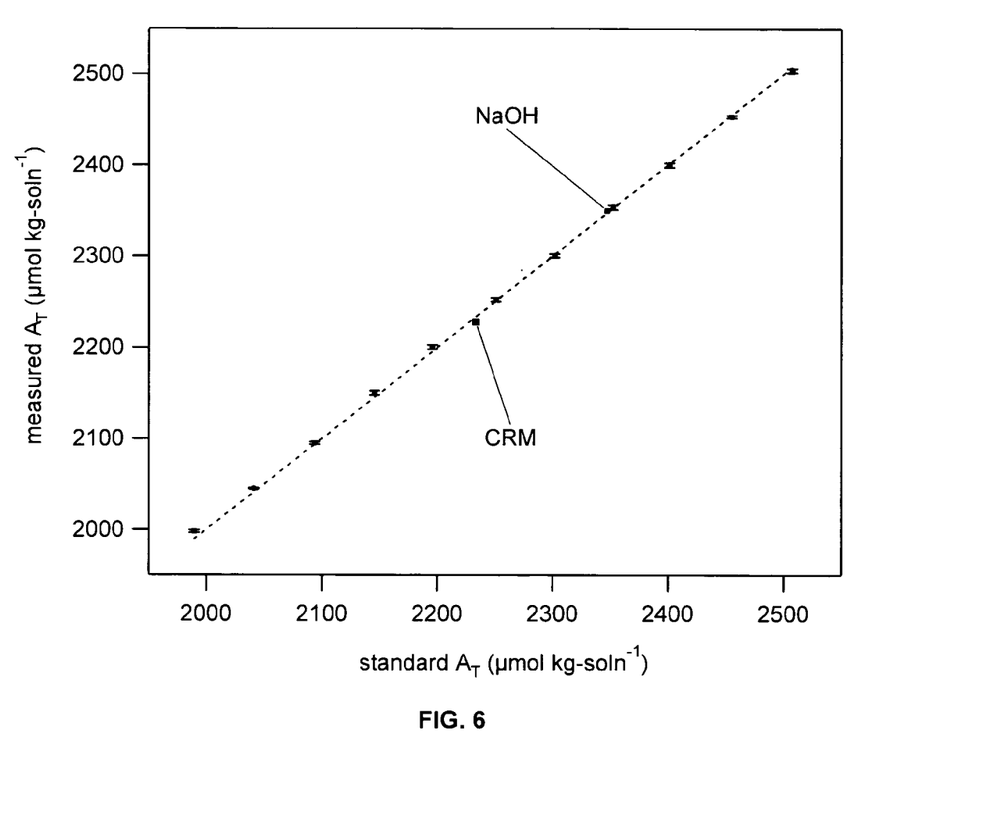
FIG. 6 presents averaged results from FIG. 5.

FIG. 5 shows the results of 279 titrations performed on 13 different samples. Eleven Na$_2$CO$_3$ standards on ~50 µmol kg-soln$^{-1}$ increments over the range 2000-2500 µmol kg-soln$^{-1}$ were analyzed. A NaOH standard and a seawater certified reference material (CRM) was also titrated, a standard widely used to verify the performance of seawater alkalinity systems (FIG. 5). The primary standard Na$_2$CO$_3$ in 0.7 mol kg-soln$^{-1}$ NaCl was used as the principal analyte in this study. A NaOH secondary standard was run to verify the accuracy. The method was also checked against a seawater CRM. FIG. 6 shows the linearity of the analysis ($R^2$=0.9999), along with 1σ error bars. Standard deviations for each sample ranged from ±0.6 to ±2.7 µmol kg-soln$^{-1}$. Based on the pooled standard deviation of 279 titrations, the 1σ precision is ±2.1 µmol kg-soln$^{-1}$ (0.1%) and accuracy is ±4.0 µmol kg-soln$^{-1}$ (~0.2%).

In this example, the subject method was used to obtain highly precise and accurate measurements with an automated titration system using low precision solenoid pumps. Rather than volume, mass or flow reproducibility, the titration performance depends instead upon spectrophotometric precision and stability. The performance of the method of the subject invention for this application currently approaches the performance of existing techniques for seawater $A_T$ titration but with a simplified apparatus.

EXAMPLE 3

Tracer Monitored Complexation Titration of Ca$^{2+}$ by EDTA Using a Spectrophotometric Tracer and Spectrophotometric Endpoint Detection The complexometric titration of Ca$^{2+}$ is commonly carried out by EDTA titration using the metal ion indicator Calmagite, which exhibits colored complexed and uncomplexed forms (Harris, 2007). A titration analogous to Example 2 can be accomplished by adding a quantitative amount of Calmagite to standardized EDTA and titrating Ca$^{2+}$. A dual wavelength measurement is used to quantify the absorbance of the complexed and uncomplexed forms of Calmagite. The total Calmagite concentration is determined from the absorbances and used in Equation 5 to determine the dilution factor. The dilution factor at the endpoint, $f_T(ep)$ is determined by titration curve analysis, as described in Example 1. The dilution factor is then used in Equation 7 to determine the calcium concentration of the sample, $[Ca^{2+}]_S$.

EXAMPLE 4

Tracer Monitored Titration Using a Potentiometric Tracer and Potentiometric Endpoint Detection The tracer used in the method of the subject invention is not limited to chromophores and some applications may prohibit the use of spectral measurements. For example, spectrophotometric detection can be degraded by a colored background matrix or the formation of precipitates. One alternative is to use a tracer that can be detected electrochemically. For example, the titration of the halides Cl$^-$, Br$^-$ and I$^-$ by silver ion, Ag$^+$, involves quantitative precipitation of the silver-halide salts AgCl(s), AgBr(s) and AgI(s) resulting in an abrupt increase in [Ag$^+$] after the equivalence point (see e.g. Harris, 2007). The classical version of this titration involves recording the volume of titrant added and activity of Ag$^+$ registered by an ion selective electrode for a series of dropwise additions of standard AgNO$_3$ titrant (Harris, 2007). A tracer monitored titration version like that of the subject invention is carried out by adding a second ion selective electrode for NO$_3^-$ which is used as a tracer for the titrant, Ag$^+$.

EXAMPLE 5

Tracer Monitored Titration Using a Tracer in the Sample

Because the dilution factors are related by $f_T+f_S=1$ (Equation 5), direct quantification of the sample dilution factor ($f_S$) can be used to calculate the titrant dilution factor ($f_T$). In this case, a tracer in the sample decreases in concentration as titrant is added. As for all titrations, the titrant concentration must be known, but the titrant dilution factor is found indirectly, by monitoring the dilution of the sample. This approach requires that either 1) a tracer is added to each sample explicitly (e.g. addition of an inert dye) or 2) the sample, by its nature, contains a practical tracer (e.g. chloride ion in seawater). The dilution factors are calculated without quantifying volume of sample by recording a background or beginning tracer value (chemical blank) when only sample is in the titration cell (i.e. when $f_S=1$).). In an optical measurement the chemical blank may be recorded as $$A = -\log_{10}\frac{I}{I_o} \qquad (13)$$

where A is optical absorbance, $I_o$ is optical intensity at the specified wavelength with titrant or titrand only in the titration chamber and I is optical intensity at the specified wavelength in said mixture of titrant and titrand. This approach does not require accurate knowledge of the tracer's physicochemical tracing property (e.g. molar absorptivity) because the blank tracer value serves as a baseline that can be used with subsequent measurements of the physical or chemical property to calculate $f_S$ by their ratio. This rule applies to the previously described titrant-based tracer approaches (Examples 1-4) if the condition is reached where $f_T=1$ (100% titrant in the titration vessel) and the tracer exists as a single chemical species when the tracer baseline is recorded.

EXAMPLE 6

Tracer Monitored Titration Using a Solid Phase Titrant-Tracer Mix

Some titrations are based on a single addition of excess titrant (beyond the endpoint) and measurement of the excess, e.g. addition of a known volume of excess acid to a weak base titrand and determination of the final pH. Because no volume or mass is measured in the subject method, excess titrant can be added in solid form, such as NaOH pellets. Prior to titration, the solid titrant is mixed with a known amount of solid tracer so that the titrant and tracer masses are accurately known. The solid tracer may be inert or act as an indicator for the extent of reaction as described in the previous examples.

The titration method of the subject invention allows accurate analysis of a sample to be conducted without requiring volumetric or gravimetric measurement of titrant or titrand. This simple method of using a tracer molecule or physical property to quantify the titrant added will make these analyses more available. The subject method can be more easily automated, is less expensive and can be conducted by inexperienced operators.

It should be understood that the examples and embodiments described herein are for illustrative purposes only and that various modifications or changes in light thereof will be suggested to persons skilled in the art and are to be included within the spirit and purview of this application and the scope of the appended claims.

OTHER REFERENCES

Almeida, C. M. N. V.; Lapa, R. A. S.; Lima, J. L. F. C.; Zagatto, E. A. G.; Araujo, M. C. U. *Anal. Chim. Acta.* 2000, 407, 213-223.

Clayton, T. D.; Byrne, R. H. *Deep-Sea Res.* 1993, 40, 2115-2129.

Dickson, A. G. *Deep Sea Res.* 1981, 28A, 609-623.

Fletcher, P. J.; van Staden, J. F. *Anal. Chim. Acta.* 2003, 485, 187-194.

Harris, D. C. *Quantitative Chemical Analysis*, 7$^{th}$ ed.; W.H. Freeman: New York, 2007.

Korn, M.; Gouveria, L. F. B. P.; de Oliveria, E.; Reis, B. F. *Anal. Chim. Acta.* 1995, 313, 177-184.

Martz, T. R.; Dickson, A. G.; DeGrandpre, M. D. *Anal. Chem.* 2006, 78, 1817-1826.

Tanaka, H.; Dasgupta, P. K.; Huang, J. *Anal. Chem.* 2000, 72, 4713-4720.

Watanabe, A.; Kayanne, H.; Nozaki, K.; Kato, K.; Negishi, A.; Kudo, S.; Kimoto, H.; Tsuda, M.; Dickson, A. G. *Mar. Chem.* 2004, 85, 75-87.

U.S. Pat. No. 4,798,803.
U.S. Pat. No. 5,618,495.
U.S. Pat. No. 6,004,822.
U.S. Pat. No. 6,082,204.
U.S. Pat. No. 6,913,672.
U.S. Pat. No. 6,913,930.

The invention claimed is:

1. A method of conducting a titration reaction wherein a tracer quantifies the relative proportions of titrant to titrand in the titration reaction, the method comprising the steps of:
   a) placing the titrand solution comprising an analyte in a mixing vessel;
   b) adding an amount of titrant solution to the titrand solution, the titrant solution comprising the tracer of a concentration $[tracer]_T$;
   c) mixing the titrant solution and titrand solution to obtain a homogeneous mixture;
   d) measuring the progress of the titrant reacting with the analyte with a detecting means;
   e) concurrently measuring a concentration of the tracer [tracer], with a tracer detecting means;
   f) determining a dilution factor wherein the dilution factor f is the ratio of total concentration of tracer in the titrant-titrand mixture $[tracer_{titrant}]_{mix}$ to tracer in the titrant $[tracer_{titrant}]_T$, $$f_T = \frac{M_T}{M_{mix}} = \frac{[tracer_{titrant}]_{mix}}{[tracer_{titrant}]_T} = \frac{[titrant]_{mix}}{[titrant]_T}$$

where $M_T$ is the amount of titrant added, $M_{mix}$ is the quantity of the titrant-titrand mixture, $[titrant]_{mix}$ is the total titrant added to the titrand, and $[titrant]_T$ is the known concentration of titrant; and
   f) performing steps b)-e) until the titration is completed;
   g) performing steps b)-f) until the titration is completed;
   h) determining the concentration of the analyte in the titrand using the dilution factor, the measurement of the progress of the titration and a titration data analysis method, wherein the tracer is a chemical species that is not consumed or produced by the titration reaction, and wherein the concentration of the analyte in the titrand is determined without quantifying the volume of the added amount of titrant solution.

2. The method of claim 1, wherein the titrant and the tracer are liquid.

3. The method of claim 1, wherein said tracer concentration is known.

4. The method of claim 1, wherein said tracer concentration is unknown and wherein said method further comprises the step of measuring a chemical blank and recording a chemical blank value for said tracer when $f_T=1$.

5. The method of claim 1, wherein said tracer is selected from the group consisting of an optical tracer, a spectrochemical tracer, an electrochemical tracer.

6. The method of claim 1, wherein said extent of reaction detecting means is selected from the group consisting of optical, spectrochemical, and electrochemical.

7. The method of claim 1, wherein said tracer detecting means is selected from the group consisting of optical, spectrochemical, and electrochemical.

8. The method of claim 1, wherein said extent of reaction detecting means and said tracer detecting means are spectrochemical means and concentrations are calculated using Beer's Law $$A = \epsilon b [C]$$

where A is absorbance at a specified wavelength, $\epsilon$ is molar absorptivity of species C over the bandpass, b is the optical pathlength in cm, and [ ] denotes concentration of species C.

9. The method of claim 8, wherein A is calculated by reference to a chemical blank where $f_S=1$ or $f_T=1$ as a starting value $$A = -\log_{10} \frac{I}{I_o}$$

where $I_o$ is optical intensity at the specified wavelength with titrant or titrand only in the titration chamber and I is optical intensity at the specified wavelength in said mixture of titrant and titrand.

10. A method of conducting a titration reaction wherein a tracer quantifies the relative proportions of titrant to titrand in the titration reaction, the method comprising the steps of:
 a) placing an amount of the titrand solution comprising an analyte in a mixing vessel, the titrand solution comprising the tracer of a concentration [tracer]$_S$;
 b) adding an amount of titrant solution of a known concentration to the titrand solution;
 c) mixing the titrant solution and titrand solution to obtain a homogeneous mixture;
 d) measuring the progress of the titration of the titrant reacting with the analyte with a detecting means;
 e) concurrently, measuring a concentration of the tracer [tracer]$_{mix}$ with a tracer detecting means;
 f) determining a dilution factor wherein the dilution factor f is the ratio of total concentration of tracer in the titrant-titrand mixture [tracer$_{titrand}$]$_{mix}$ to tracer in the titrand [tracer$_{titrand}$]$_S$, $$f_S = \frac{M_S}{M_{mix}} = \frac{[\text{tracer}_{titrand}]_{mix}}{[\text{tracer}_{titrand}]_S} = 1 - \frac{[\text{titrant}]_{mix}}{[\text{titrant}]_T}$$

where $M_S$ is the amount of titrand and $M_{mix}$ is the quantity of the titrant-titrand mixture; and
 g) performing steps b)-f) until the titration is completed;
 h) determining the concentration of the analyte in the titrand using the dilution factor, the measurement of the progress of the titration and a titration data analysis method,
wherein the tracer is a chemical species that is not consumed or produced by the titration reaction.

11. The method of claim 10, wherein said tracer concentration is known.

12. The method of claim 10, wherein said tracer concentration is unknown and wherein said method further comprises the step of measuring a chemical blank and recording a chemical blank value for said tracer when $f_S=1$.

13. The method of claim 10, wherein the titrant and the tracer are liquid.

14. The method of claim 10, wherein said tracer is selected from the group consisting of an optical species, a spectrochemical species, an electrochemical species and a physical species.

15. The method of claim 10, wherein said extent of reaction detecting means is selected from the group consisting of optical, spectrochemical, electrochemical, and physical means.

16. The method of claim 10, wherein said tracer detecting means is selected from the group consisting of optical, spectrochemical, electrochemical, and physical means.

17. The method of claim 10, wherein said extent of reaction detecting means and said tracer detecting means are spectrochemical means and concentrations are calculated using Beer's Law $$A = \epsilon b [C]$$

where A is absorbance at a specified wavelength, $\epsilon$ is molar absorptivity of species C over the bandpass, b is the optical pathlength in cm, and [ ] denotes concentration of species C.

18. The method of claim 17, wherein A is calculated by reference to a chemical blank where $f_S=1$ or $f_T=1$ as a starting value $$A = -\log_{10} \frac{I}{I_o}$$

where $I_o$ is optical intensity at the specified wavelength with titrant or titrand only in the titration chamber and I is optical intensity at the specified wavelength in said mixture of titrant and titrand.

19. A method of conducting a titration reaction wherein a tracer, being an indicator for the titration reaction, quantifies the relative proportions of titrant to titrand in the titration reaction, the method comprising the steps of:
 a) placing the titrand solution comprising an analyte in a mixing vessel;
 b) adding an amount of titrant solution to the titrand solution, the titrant solution comprising the tracer of a concentration [tracer]$_T$;
 c) mixing the titrant solution and titrand solution to obtain a homogeneous mixture;
 d) measuring a concentration of the tracer [tracer]$_{mix}$ with a tracer detecting means and using the concentration of the tracer to measure the progress of the titration;
 e) determining a dilution factor wherein the dilution factor f is the ratio of total concentration of tracer in the titrant-titrand mixture [tracer$_{titrant}$]$_{mix}$ to tracer in the titrant [tracer$_{titrant}$]$_T$, $$f_T = \frac{M_T}{M_{mix}} = \frac{[\text{tracer}_{titrant}]_{mix}}{[\text{tracer}_{titrant}]_T} = \frac{[\text{titrant}]_{mix}}{[\text{titrant}]_T}$$

where $M_T$ is the amount of titrant added, $M_{mix}$ is the quantity of the titrant-titrand mixture, [titrant]$_{mix}$ is the total titrant added to the titrand, and [titrant]$_T$ is the known concentration of titrant; and
 f) performing steps b)-e) until the titration is completed;
 g) determining the concentration of the analyte in the titrand using the dilution factor, the measurement of the progress of the titration and a titration data analysis method, wherein the tracer is a chemical species that is not consumed or produced by the titration reaction, and wherein the concentration of the analyte in the titrand is determined without quantifying the volume of the added amount of titrant solution.

20. A method of conducting a titration reaction wherein a tracer, being an indicator for the titration reaction, quantifies the relative proportions of titrant to titrand in the titration reaction, the method comprising the steps of:
   a) placing an amount of the titrand solution comprising an analyte in a mixing vessel, the titrand solution comprising the tracer of a concentration $[tracer]_s$;
   b) adding an amount of titrant solution of a known concentration to the titrand solution;
   c) mixing the titrant solution and titrand solution to obtain a homogeneous mixture;
   d) measuring a concentration of the tracer $[tracer]_{mix}$ with a tracer detecting means and using the concentration of the tracer to measure the progress of the titration;
   e) determining a dilution factor wherein the dilution factor f is the ratio of total concentration of tracer in the titrant titrand mixture $[tracer_{titrand}]_{mix}$ to tracer in the titrand $[tracert_{titrand}]_s$, $$f_S = \frac{M_S}{M_{mix}} = \frac{[tracer_{titrand}]_{mix}}{[tracer_{titrand}]_S} = 1 - \frac{[titrant]_{mix}}{[titrant]_T}$$

where $M_s$ is the amount of titrand and $M_{mix}$ is the quantity of the titrant-titrand mixture; and
   f) performing steps b)-e) until the titration is completed;
   g) determining the concentration of the analyte in the titrand using the dilution factor, the measurement of the progress of the titration and a titration data analysis method,
wherein the tracer is a chemical species that is not consumed or produced by the titration reaction, and wherein the concentration of the analyte in the titrand is determined without quantifying the volume of the added amount of titrant solution.

* * * * *